United States Patent [19]

Sakai et al.

[11] Patent Number: 5,254,694

[45] Date of Patent: Oct. 19, 1993

[54] OPTICALLY ACTIVE EPOXYCYCLOHEXANE DERIVATIVE AND EPOXYCYCLOHEXANONE DERIVATIVE, AND PROCESS FOR THE PREPARATION THEREOF

[75] Inventors: Kunikazu Sakai, Setagaya; Kyoko Takahashi, Yokohama, both of Japan

[73] Assignee: Sagami Chemical Research Center, Tokyo, Japan

[21] Appl. No.: 834,547

[22] PCT Filed: Aug. 16, 1990

[86] PCT No.: PCT/JP90/01042

§ 371 Date: Feb. 12, 1992

§ 102(e) Date: Feb. 12, 1992

[87] PCT Pub. No.: WO91/02728

PCT Pub. Date: Mar. 7, 1991

[30] Foreign Application Priority Data

Aug. 18, 1989 [JP] Japan .................. 1-211290
Aug. 25, 1989 [JP] Japan .................. 1-217221
Apr. 12, 1990 [JP] Japan .................. 2-95007

[51] Int. Cl.⁵ .................. C07D 303/32; C07D 301/00
[52] U.S. Cl. .................. 549/546; 549/513; 549/539; 549/545
[58] Field of Search .................. 549/546

[56] References Cited

U.S. PATENT DOCUMENTS 3,400,158  9/1968  Roberts .................. 549/546
3,567,743  3/1971  Anderson .................. 549/513

OTHER PUBLICATIONS

Acemoglu et al. "Helvetica Chimica Acta" vol. 71, No. 5, (1988), pp. 931–956.

*Primary Examiner*—Joseph E. Evans
*Attorney, Agent, or Firm*—Wenderoth, Lind & Ponack

[57] ABSTRACT

An optically active epoxycyclohexane derivative represented by the general formula:

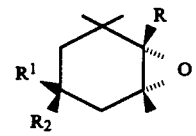

wherein R represents a 4-oxycarbonyl-1-hydroxy-3-methyl-3(Z)-buten-1-yl or 4-hydroxycarbonyl-3-methyl-1(E),3(Z)-butadien-1-yl group; and $R^1$ and $R^2$ each represent a lower alkoxy group or together form a 1,3-dioxolane ring together with the carbon atom to which they are bonded, and an enantiometer thereof.

An optically active epoxycyclohexanone derivative represented by the general formula:

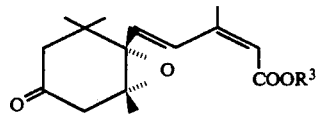

wherein $R^3$ represents a hydrogen atom or a lower alkyl, allyl, aralkyl or aryl group, and an enantiomer thereof.

Further, the process for preparing these compounds, is also disclosed.

1 Claim, No Drawings

OPTICALLY ACTIVE EPOXYCYCLOHEXANE DERIVATIVE AND EPOXYCYCLOHEXANONE DERIVATIVE, AND PROCESS FOR THE PREPARATION THEREOF

TECHNICAL FIELD

The present invention relates to an optically active epoxycyclohexane derivative represented by the following general formula (I):

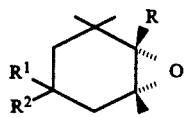

wherein R represents a 4-oxycarbonyl-1-hydroxy-3-methyl-3(Z)-buten-1-yl or 4-hydroxycarbonyl-3-methyl-1(E),3(Z)-butadien-1-yl group; and $R^1$ and $R^2$ each represent a lower alkoxy group or together form a 1,3-dioxolane ring together with the carbon atoms to which $R^1$ and $R^2$ are bonded,
and an enantiomer thereof; an optically active epoxycyclohexanone derivative represented by the general formula (II):

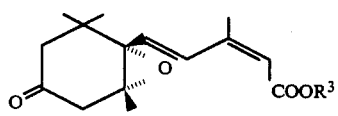

wherein $R^3$ represents a hydrogen atom or
a lower alkyl, allyl, aralkyl or aryl group, which is derived from an optically active epoxycyclohexane derivative represented by the general formula (I), and an enantiomer thereof; and a process for the preparation of a compound represented by the above general formula (I) wherein R is a 4-hydroxycarbonyl-3-methyl-1(E),3(Z)-butadien-1-yl group.

The optically active epoxycyclohexane derivative (I) and its enantiomer and optically active epoxycyclohexanone derivative (II) and its enantiomer according to the present invention serve as important intermediates for the preparation of abscisic acid represented by the following formula (III) which has not been applied to agriculture as yet in spite of its important activity on plant physiology as a plant hormone, so that the utilization thereof in the feature is expected, and xanthoxin represented by the following formula (IV) which is more difficultly available than abscisic acid and therefore has not been applied to agricultural production in spite of its activity equivalent to that of abscisic acid, in the form of a natural type optical isomer or an enantiomer thereof:

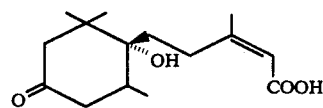

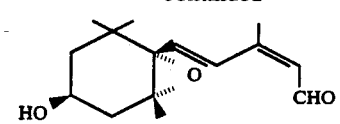

BACKGROUND ART

Up to this time, several processes for preparing optically active abscisic acid have been known. These processes are classified into (i) a group of processes characterized by using an optically active raw material (see K. Mori, Tetrahedron Lett., 1973, 2635; M. Shibasaki, S. Terashima and S. Yamada, Chem. Pharm. Bull., 1976, 24, 315; and K. Kienzle, H. Mayer, R. E. Minder and H. Thommen, Helv. Chim. Acta, 1978, 61, 2616), (ii) a group of fermentation processes using a microorganism [see Japanese Patent Laid-Open No. 36393/1983 and the abstracts of the 30th Symposium on the Chemistry of Natural Products (Fukuoka, 1988), p.332 ] and (iii) a group of processes comprising preparing racemic abscisic acid which is not optically active and separating the racemic modification into optically active isomers by optical resolution (see R. S. Burden and H. F. Taylor, Pure & Appl. Chem., 1976, 47, 203).

However, the processes of the group (i) are disadvantageous in that the optically active raw material is generally difficultly available and the fermentation processes of the group (ii) are unfit for practical use owing to their low productivity. The optical resolution processes of the group (iii) have disadvantages due to optical resolution in that the operation is troublesome and the objective optically active substance can be obtained only in a low yield even by following a process using an optically inactive racemic modification of a compound represented by the general formula (VI) or (VII) which will be described below as an intermediate (see M. G. Constantino, P. Losco and E. E. Castellano, J. Org. Chem., 1989, 54, 681), which process is one of the most efficient processes among known processes for preparing a racemic modification.

Although optically active abscisic acid is demanded because of its higher activity as a plant hormone than that of racemic one (see R. S. Burden and H. F. Taylor, Pure & Appl. Chem., 1976, 47, 203), optically active abscisic acid is now much more expensive than racemic one.

On the other hand, not a few processes for preparing xanthoxin have also been known. For example, there have been known a process (i) characterized by using β-ionone as a starting material (see R. S. Burder, G. W. Dawson and H. F. Taylor, Phytochem., 1972 11, 2295 and H. F. Taylor and R. S. Burder, J. Exp. Bot., 1973, 24, 873) and a process (ii) characterized by using isophorone as a starting material (see T. Oritani and K. Yamashita, Agr. Biol. Chem., 1973, 37, 1215). However, the processes (i) and (ii) are ones for preparing optically inactive racemic xanthoxin, being unimportant. Further, although a process (iii) for preparing optically active xanthoxin from an optically active 4-hydroxycyclocitral as a starting material has been also known (see F. Kienzle, H. Mayer, R. E. Minder and H. Thommen, Helv. Chim. Acta, 1978, 61, 2616), this process is also disadvantageous in that the optically active starting material is difficultly available.

DISCLOSURE OF INVENTION

The inventors of the present invention have found that an optically active epoxycyclohexane derivative represented by the general formula (I) and an optically active epoxycyclohexanone derivative represented by the general formula (II) can be efficiently prepared from an easily available asymmetric epoxy aldehyde represented by the general formula (V) which will be described below as a starting material and that optically active abscisic acid represented by the formula (III) and optically active xanthoxin represented by the formula (IV) can be prepared from the above optically active epoxycyclohexane or epoxycyclohexanone derivative in a few steps. The present invention has been accomplished on the basis of these findings.

The epoxycyclohexane derivative represented by the general formula (I) and the epoxycyclohexanone derivative represented by the general formula (II) can be prepared via the following steps 1 to 4.

Further, optically active abscisic acid (III) and optically active xanthoxin (IV) can be easily prepared from the compound represented by the general formula (I) or (II) via the following steps A to F.

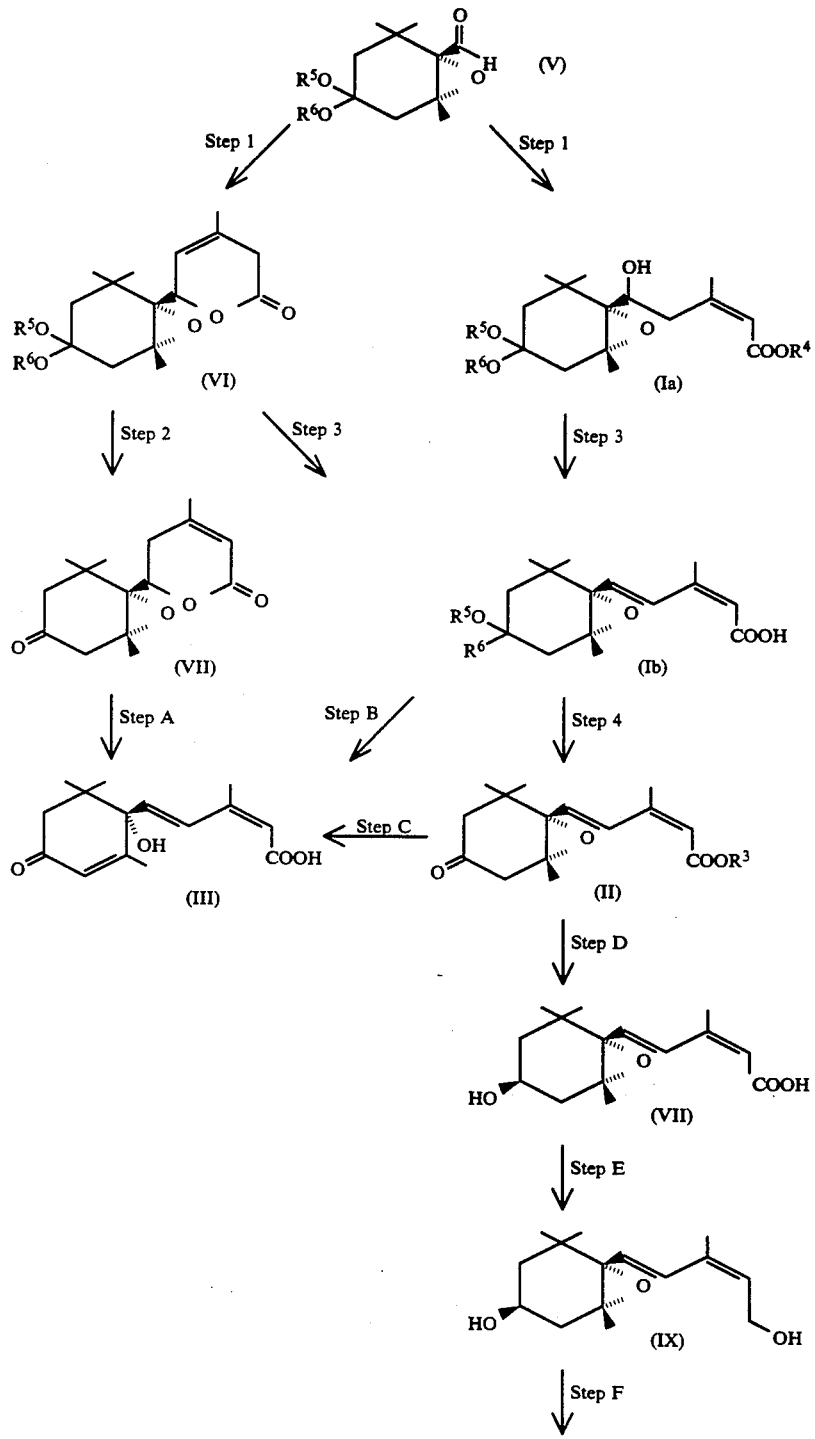

-continued

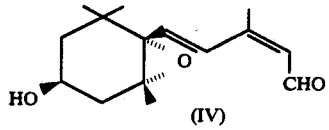
(IV)

wherein $R^3$ represents a hydrogen atom or a lower alkyl, allyl, aralkyl or aryl group; $R^4$ represents a lower alkyl, allyl, aralkyl or aryl group; $R^5$ and $R^6$ each represent a lower alkyl group or together form a dioxolane ring together with the carbon atoms to which $R^5$ and $R^6$ are bonded.

Although the general formulas (Ia), (Ib) and (II) show respective compounds each in the form of one optical isomer, the same relationship can apply to the enantiomers of the isomers.

The above steps will now be described successively in detail.

Step 1

In this step, an optically active aldehyde represented by the general formula (V) is reacted with a 3-(halomethyl)-3-methylacrylic ester in the presence of zinc to give an optically active 4,4-dialkoxy-1-(5,6-dihydro-2H-4-methyl-2-oxopyran-6-yl)-1,2-oxo-2,6,6-trimethylcyclohexane represented by the general formula (VI) and an optically active 4,4-dialkoxy-1-[4-(alkoxycarbonyl)-1-hydroxy-3-methyl-3-buten-1-yl]-1,2-oxo-2,6,6-trimethylcyclohexane represented by the general formula (Ia). In the general formula (V), $R^5$ and $R^6$ may be each a methyl, ethyl, n- or i-propyl or n-, i-, sec- or t-butyl group. $R^5$ and $R^6$ need not always be the same. Further, $R^5$ and $R^6$ may together form a 1,3-dioxa ring together with the carbon atoms to which they are bonded and it is preferable from the standpoint of stability and hydrolyzability that the ring be a 1,3-dioxolane ring derivative. On the other hand, in the 3-(halomethyl)-3-methylacrylic ester to be used in this step, X may be a chlorine, bromine or iodine atom. Particularly, such an ester wherein X is a bromine atom is preferable because of its easiness in preparation and its high reactivity. Further, the $R^4$ group constituting the ester includes lower alkyl groups such as methyl, ethyl n- and i-propyl and n-, i-, sec- and t-butyl groups; substituted and unsubstituted allyl groups; aralkyl groups such as benzyl, p-methoxybenzyl and p-nitrobenzyl groups; and phenyl and substituted phenyl groups. The 3-(bromomethyl)-3-methylacrylic ester which is one of the raw material to be used in this step is known to be easily preparable by brominating a 3,3-dimethylacrylic ester (see I. Ahmad, R. N. Gedye and A. Nechvatal, J. Chem. Soc. (C), 1968, 185). Further, the aldehyde represented by the general formula (V) which is the other raw material is also known to be easily preparable through asymmetric epoxidization in the form of an optically active substance (see M. Acemoglu, P. Uebelhart, M. Rey and C. H. Eugster, Helv. Chim. Acta, 1988, 71, 931 and the Referential Examples which will be described below).

The condensation is conducted under so-called Reformatsky reaction conditions. In conducting the condensation practically, it is necessary to use zinc in an amount of 1.0 to 5.0 equivalents, preferably 2.0 to 3.0 equivalents. It is suitable that the 3-(bromomethyl)-3-methylacrylic ester be used in an amount of 1.2 to 1.5 equivalents. The condensation is preferably conducted in a solvent such as ether, tetrahydrofuran, dioxane, benzene or toluene. The reaction temperature is 0° to 150° C., preferably 20° to 50° C. The reaction of this step gives a mixture comprising a lactone compound (VI) which is a cyclization product and an ester (Ia), which can be easily separated by a suitable means such as column chromatography.

Step 2

In this step, an optically active acetal represented by the general formula (VI) is converted into optically active 1-(5,6-dihydro-2H-4-methyl-2-oxopyran-6-yl)-1,2-oxo-2,6,6-trimethylcyclohexan-4-one represented by the formula (VII) by treatment with an acid. This treatment is conducted under mildly acid conditions, wherein a dilute solution of hydrochloric, sulfuric, phosphoric, camphorsulfonic, or methanesulfonic acid or an organic acid such as formic, acetic or oxalic acid may be used. The solvent to be used in this step includes water; alcohols such as methanol and ethanol; water-soluble ethers such as THF and dioxane; and mixtures of two or more of them. Alternatively, the treatment may be conducted in a two-layer or two-phase system comprising an aqueous acid solution or a silica gel containing an acid adsorbed thereon and a water-incompatible solvent such as methylene chloride, chloroform, benzene or ether. Generally, neither heating nor cooling is particularly necessary for the treatment.

Step 3

In this step, the optically active lactone or ester represented by the general formula (VI) or (Ia) which has been prepared in the above Step 1 is converted into an optically active 4,4-dialkoxy-1-[4-(oxycarbonyl)-3-methyl-1,3-butadien-1-yl]-1,2-oxo-2,6,6-trimethylcyclohexane represented by the general formula (Ib) by treatment with a base. The base to be used in this step includes hydroxides of alkali and alkaline earth metals, such as sodium hydroxide, potassium hydroxide, lithium hydroxide and barium hydroxide; alkali metal carbonates such as sodium carbonate and potassium carbonate; quaternary ammonium hydroxides such as benzyltrimethylammonium hydroxide; alkali metal alkoxides such as sodium methoxide, sodium ethoxide, sodium t-butoxide and potassium t-butoxide; and ammonia. The solvent to be used in this step includes water, methanol, ethanol, ether, THF, dioxane, pyridine and mixtures of two or more of them.

Step 4

In this step, an optically active diene acetal represented by the general formula (Ib) is converted into 1-[4-(oxycarbonyl)-3-methyl-1,3-butadien-1-yl]-1,2-oxo-2,6,6-trimethylcyclohexan-4-one represented by the general formula (II) by treatment under mildly acid conditions. The acid to be used in this step includes hydrochloric, sulfuric, phosphoric, camphorsulfonic, methanesulfonic and perchloric acids. In order to avoid the concurrence of Step C, the treatment must be conducted either with a dilute acid or at a low temperature. The object of avoiding the concurrence of Step C can be easily attained by treating the acetal (Ib) with 1 to 10% perchloric acid under cooling with ice.

Optically active abscisic acid can be prepared from the compound (Ib) or (II) thus prepared according to the present invention via Step B or C which will be described below. Further, optically active abscisic acid can be also prepared from the compound (VII) which has been found separately by the inventors of the present invention via the following Step A.

Step A

In this step, the optically active keto epoxide represented by the formula (VII) is converted into optically active abscisic acid represented by the formula (III) by treatment with a base. In this step, the process described in the above Step 3 can be used as such.

The abscisic acid (III) prepared from the intermediate represented by the formula (VII) exhibits positive optical rotation and has the same absolute configuration as that of natural one (see F. Kienzle, Mayer, R. E. Minder and H. Thommen, Helv. Chim. Acta, 1978, 61, 2616).

Step B

In this step, an optically active acetal represented by the general formula (Ib) is converted into abscisic acid represented by the formula (III) by treatment with an acid.

In conducting this step, the process described in the above Step 2 can be used as such.

Step C

In this step, an optically active cyclohexanone represented by the general formula (II) is converted into abscisic acid represented by the formula (III) by treatment with an acid. In conducting this step, the process described in the above Step B can be used as such.

Further, optically active xanthoxin can be prepared from the compound represented by the general formula (II) via the following Steps D, E and F.

Step D

In this step, the keto group of an epoxycyclohexanone derivative represented by the general formula (II) is selectively reduced into a hydroxyl group to give a 1-[4-(oxycarbonyl)-3-methyl-1,3-butadien-1-yl]-4-hydroxy-1,2-oxo-2,6,6-trimethylcyclohexane represented by the general formula (VIII). Preferable examples of the reducing agent to be used in this step include sodium borohydride, lithium aluminum hydride, diisobutylaluminum hydride, K-SELECTRIDE ®, and L-SELECTRIDE ®. The reduction is conducted in a solvent suitably selected from among water, methanol, ethanol, ethyl ether, tetrahydrofuran, toluene and mixtures of two or more of them depending upon the reducing agent used.

The substances of the general formula (VIII) which are the products in this step have already been known and the preparation of optically active xanthoxin therefrom has already been accomplished (see F. Kienzle, H. Mayer, R. E. Minder and H. Thommen, Helv. Chim. Acta, 1978, 61, 2616).

Step E

In this step, an epoxycyclohexanol derivative represented by the general formula (VIII) is further reduced into 1-(5-hydroxy-3-methyl-1,3-pentadien-1-yl)-4-hydroxy-1,2-oxo-2,6,6-trimethylcyclohexane represented by the formula (IX). The reduction in this step is conducted under the conventional conditions for reducing a carboxyl or ester group into a hydroxymethyl group. For example, lithium aluminum hydride or diisobutylaluminum hydride is preferably used as a reducing agent in the reduction. The reduction is conducted in a solvent suitably selected from among ethyl ether, tetrahydrofuran, toluene and mixtures of two or more of them depending upon the reducing agent used.

By treating an epoxycyclohexanone derivative represented by the general formula (II) with an excess of a reducing agent under the conditions employed in this strip, the diol derivative represented by the formula (IX) can be obtained without isolating an intermediate represented by the general formula (VIII). In other words, the Steps D and E can be conducted at a stroke.

The diol derivative of the formula (IX) which is a product in this step is a known substance and the preparation of optically active xanthoxin therefrom has already been accomplished (see F. Kienzle, H. Mayer, R. E. Minder and H. Thommen, Helv. Chim. Acta, 1978, 61, 2616).

Step F

In this step, the diol represented by the formula (IX) is converted into optically active xanthoxin through the selective oxidation of the primary hydroxyl group into an aldehyde group. The oxidizing agent to be used in the selective oxidation is preferably active manganese dioxide.

The reaction conditions for such selective oxidation have already been known and can be applied as such to this step (see F. Kienzle, H. Mayer, R. E. Minder and H. Thommen, Helv. Chim. Acta. 1978, 61, 2616).

BEST MODE FOR CARRYING OUT THE INVENTION

The present invention will now be described in more detail by referring to the following Examples and Referential Examples.

REFERENTIAL EXAMPLE 1

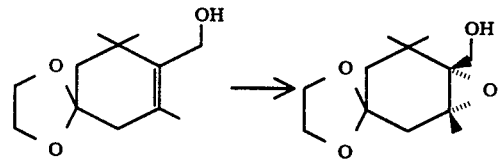

80 mg of powdery molecular sieves 3A was added to 8 ml of anhydrous methylene chloride in an argon atmosphere. The obtained mixture was cooled to −20° C., followed by the addition of 39 μl (15 mole %) of D-(−)-diethyl tartrate (DET) and 43 μl (10 mole %) of tetraisopropoxytitanium. 378 μl (1.63 mmol) of a 2.4M solution of t-butyl hydroperoxide (TBHP) in isooctane was dropped into the mixture obtained above. After 45 minutes, a solution of 314 mg (1.4 mmol) of 4,4-ethylenedioxy-2,6,6-trimethyl-1-cyclohexenemethanol in anhydrous methylene chloride (0.5 ml) was dropped into the resulting mixture. After 4.5 hours, 900 μl of distilled water and 1.5 ml of a 10% solution of sodium hydroxide in a saturated aqueous solution of sodium chloride were added to the resulting mixture successively. After one hour, the methylene chloride layer was recovered and the aqueous layer was extracted with methylene chloride. The methylene chloride layers were combined, dehydrated over anhydrous sodium sulfate and distilled in a vacuum to remove the solvent. 351 mg of a crude product was obtained. This crude product was purified by silica gel column chromatography (hexane/ethyl acetate=7:1) to give 252 mg (75%) of objective 4,4-ethylenedioxy-1,2-oxo-2,6,6-trimethylcyclohexanemethanol. 20 mole % of a shift reagent Eu(tfc)₃ was added to the pure product and the obtained mixture was subjected to H-NMR spectroscopy. The optical yield was about 90%.

$^{1}$H-NMR(CDCl$_3$): δ   1.09(s,3H),   1.17(s,3H), 1.32(dd,1H,J=2.3,13.8),   1.41.(s,3H), 1.63(d,1H,J=13.8),   1.87(t.1H,J=5.1), 2.00(dd,1H,J=2,3,15.6),   2.25(d,1H,J=15.6), 3.71(dd,1H,J=4.9,11.3), 3.77~3.91(m,4H+1H).

MS: 229(m+1) 213(M—OH).

$[α]_D^{20}$:+19.5 (CO.84, CHCl$_3$).

REFERENTIAL EXAMPLE 2

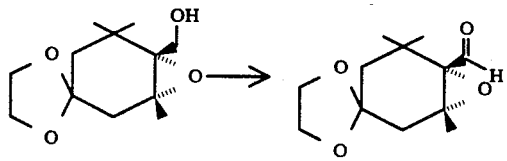

140 μl (1.59 mmol, 1.1 equivalents) of oxalyl chloride and 225 μl (3.13 mmol, 2.2 equivalents) of anhydrous dimethyl sulfoxide (DMSO) were dissolved in 7 ml of anhydrous methylene chloride in an argon atmosphere. After 10 minutes, a solution of 329 mg (1.442 mmol) of 4,4-ethylenedioxy-1,2-oxo-2,6,6-trimethylcyclohexanemethanol in 2 ml of anhydrous methylene chloride was dropped into the solution prepared above. After 20 minutes, 1.5 ml (10.8 mmol, 7.5 equivalents) of triethylamine was added to the resulting mixture. Further, after 10 minutes, distilled water was added to the resulting mixture to give an anhydrous methylene chloride layer and an aqueous layer. The methylene chloride layer was recovered and the aqueous layer was extracted with methylene chloride. The methylene chloride layers were combined, dehydrated over anhydrous sodium sulfate and distilled in a vacuum to remove the solvent. 322 mg (99%) of 4,4-ethylenedioxy-1,2-oxo-2,6,6-trimethylcyclohexanecarboxaldehyde was obtained.

$^{1}$H-NMR(CDCl$_3$): δ   1.08(s,3H),   1.31(s,3H), 1.32(dd,1H,J=1.9,13.8), 1.46(s,3H), 1.71(d,1H,J=13.8), 2.09(dd,1H,J=1.9,15.8),   2.30(d,1H,J=15.8), 3.82~3.90(m,2H), 3.91~3.95(m,2H), 9.78(s,1H).

EXAMPLE 1

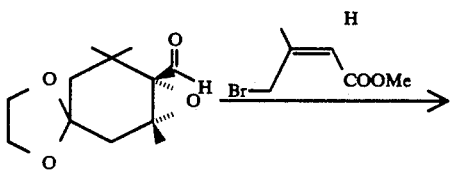

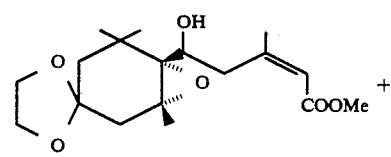

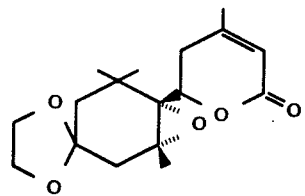

200 mg (4 equivalents) of powdery zinc activated by the process described in Reagents for Organic Synthesis vol.1, p.1285 and 10 mg of iodine were put in an argon atmosphere, followed by the addition of 1.5 ml of anhydrous THF. The obtained mixture was cooled with ice, followed by the addition of 313 mg (1.58 mmol, 2 equivalents) of methyl 3-(bromomethyl)-3-methylacrylate (Z/E=4:5). The obtained mixture was stirred for 10 minutes, followed by the dropwise addition of a solution of 178 mg (0.79 mmol) of the aldehyde ($[α]_D^{20}$-56.7 (CO.98, CHCl$_3$)) prepared in the Referential Example 2 in 1.5 ml of anhydrous THF. After 30 minutes, the disappearance of the raw material was ascertained, followed by the addition of 5 ml of a saturated aqueous solution of ammonium chloride. The obtained mixture was extracted with diethyl ether. The organic layer was washed with a saturated aqueous solution of common salt, dehydrated over anhydrous sodium sulfate and distilled in a vacuum to remove the solvent. 303 mg of a crude product was obtained. This crude product was purified by silica gel column chromatography (hexane/ethyl acetate=6:1) to isolate an isomeric mixture of 4,4-ethylenedioxy-1-{4-(methoxycarbonyl)-1-hydroxy-3-methyl-3-buten-1-yl}-1,2-oxo-2,6,6-trimethylcyclohexane in an amount of 51 mg (19%) and two isomers (lactones 1 and 2) of 4,4-ethylenedioxy-1-(5,6-dihydro-2H-4-methyl-2-oxopyran-6-yl)-1,2-oxo-2,6,6-trimethylcyclohexane in amounts of 44 mg (18%) and 68 mg (28%), respectively.

methyl ester mixture $^{1}$H-NMR(CDCl$_3$):   δ   1.08(s,3H),   1.20(s,3H), 1.31(dd,1H,J=2.5,14),   1.52(s,3H),   1.60(d,1H,J=14), 1.97(d,1H,J=2.5),   2.19(dd,1H,J=2.5,16), 2.28(d,3H,J=1.3),   2.41~2.51(m,2H),   2.59(s,1H), 3.69(s,3H),   3.82~3.94(m,4H),   4.25(m,1H),   5.80(dd, 1H,J=1.1,2.4).

$[α]_D^{20}$:+35.7 (CO.83, CHCl$_3$).

lactone 1 mp: 157.5~161° C.

$^{1}$H-NMR(CDCl$_3$):   δ   1.00(s,3H),   1.30(dd,1H, J=2.0,13.7), 1.31(s,3H), 1.42(s,3H), 1.67(d,1H,J=13.7), 1.99(dd,1H,J=4.7,19.1),   1.99(s,3H), 2.07(dd,1H,J=2.0,15.8),   2.21(d,1H,J=15.8), 2.62(qdd,1H,J=1.2,   13.5,19.1),   3.78~3.96(m,4H), 5.04(dd, 1H,J=4.7,13.5), 5.79(d,1H,J=1.5).

MS: 308(M+)197 181 113 112 111 86.

$[α]_D^{20}$:+38.1 (CO.62, CHCl$_3$).

lactone 2

$^{1}$H-NMR(CDCl$_3$):   δ   1.21(s,3H),   1.34(dd,1H, J=1.6,13.7), 1.35(s,3H), 1.44(s,3H), 1.69(d, 1H,J=13.7), 2.02(t,3H,J=1.2),   2.10(dd,1H,J=1.6,15.7),   2.24(d,1H, J=15.7),   2.36(dd,1H,J=3.7,17.5), 2.87(qdd,1H,J=1.2,13.5,17.5),   3.83~3.93(m,4H), 4.52(dd,1H,J=3.7,13.5), 5.81(dd,1H,J=1.4,2.3).

$[α]_D^{20}$:−59.7 (Cl.02,CHCl$_3$).

EXAMPLE 2

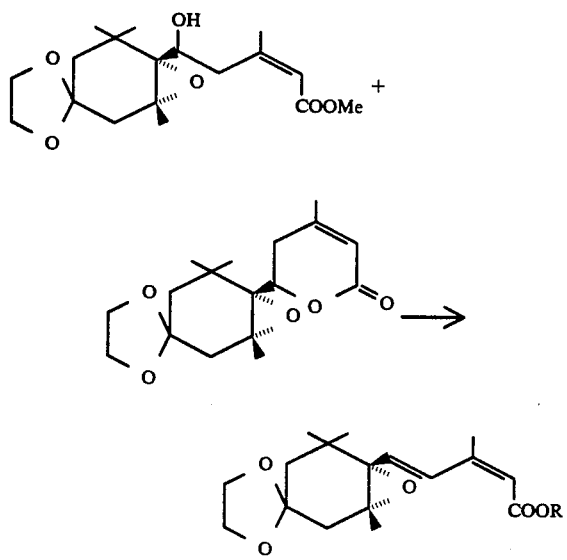

716 mg (2.5 equivalents) of potassium methoxide was dissolved in 30 ml of absolute methanol in an argon atmosphere at 0° C., followed by the dropwise addition of a solution of 765 mg (2.5 mmol) of a mixture comprising 4,4-ethylenedioxy-1-(5,6-dihydro2H-4-methyl-2-oxopyran-6-yl)-1,2-oxo-2,6,6-trimethylcyclohexane and two isomers of 4,4-ethylenedioxy1-{4-(methoxycarbonyl)-1-hydroxy-3-methyl-3-buten1-yl}-1,2-oxo-2,6,6-trimethylcyclohexane (prepared in a similar manner to that of the Example 1) in 10 ml of absolute methanol. The obtained mixture was stirred at a room temperature for 2 hours to conduct a reaction. In order to accelerate the reaction, the mixture was heated to 60° C. and stirred for 2 hours. The reaction mixture was neutralized with a saturated aqueous solution of ammonium chloride, followed by the addition of a small amount of 2N hydrochloric acid. The obtained mixture was extracted with diethyl ether. The organic layer was washed with a saturated aqueous solution of sodium chloride, dehydrated over anhydrous sodium sulfate and distilled in a vacuum to remove the solvent. 688 mg (92%) of 4,4-ethylenedioxy-1-{4-(hydroxycarbonyl)-3-methyl-1,3-butadien-1-yl}-1,2-oxo-2,6,6-trimethylcyclohexane was obtained. This product was treated with diazomethane to give a methyl ester quantitatively.

carboxylic acid $^1$H-NMR(CDCl$_3$): δ  1.00(s,3H),  1.21(s,3H), 1.25(s,3H), 1.35(dd,1H,J=2.0,13.7), 1.74(d,1H,J=13.7), 2.05(d,1H,J=1.2),  2.05(dd,1H,J=2.0,15.7), 2.28(d,1H,J=15.7), 3.82~3.96(m,4H), 5.72(d,1H,J=1.1), 6.34(dd,1H,J=0.5,16.0), 7.63(dd,1H, J=0.7,16.0).

[α]$_D^{20}$: +19.9 (Cl.01, CHCl$_3$).

methyl ester $^1$H-NMR(CDCl$_3$): δ  1.00(s,3H),  1.22(s,3H), 1.25(s,3H) 1.34(dd,1H,J=2.2,14), 1.74(d,1H,J=14), 2.01(s,3H), 2.04(dd, 1H,J=2.2,16), 2.28(d,1H,J=16), 3.70(s,3H), 3.82~3.95(m,4H), 5.70(brs,1H), 6.28(d,1H,J=16), 7.62(d,1H,J=16).

EXAMPLE 3

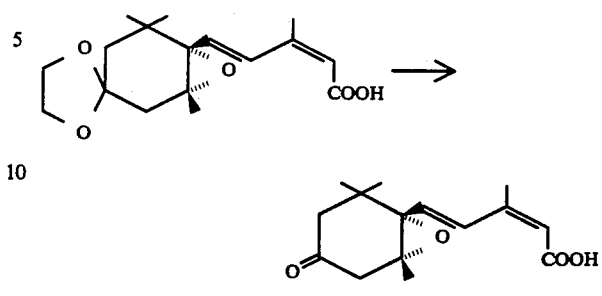

11 mg (0.036 mmol) of 4,4-ethylenedioxy-1-{4-(hydroxycarbonyl)-3-methyl-1,3-butadien-1-yl}-1,2-oxo-2,6,6-trimethylcyclohexane was dissolved in 100 μl of a 10% solution of perchloric acid in a THF/H$_2$O (1:1) mixture at 4° C. The obtained solution was stirred for 2 hours and neutralized with a saturated aqueous solution of sodium hydrogencarbonate. The resulting mixture was extracted with methylene chloride. The organic layer was washed with water, dehydrated over anhydrous sodium sulfate and distilled in a vacuum to remove the solvent. 8.7 mg (92%) of 1-{4-(hydroxycarbonyl)-3-methyl-1,3-butadien-1-yl}-1,2-oxo-2,6,6-trimethylcyclohexan-4-one was obtained.

$^1$H-NMR(CDCl$_3$): δ  1.08(s,3H),  1.16(s,3H), 1.27(s,3H),  1.98(d,1H,J=15),  2.20(d,3H, J=5.3), 2.60(dd,1H,J=1.1,20),  2.63(d,1H,  J=15), 2.87(d,1H,J=20),  5.78(brs,1H),  6.32(d,1H,J=16), 7.72(d,1H,J=16).

IR(KBr disk): 3450, 2980, 1718, 1676, 1246 cm$^{-1}$.

[α]$_D^{20}$:+115.8(CO.81, CHCl$_3$).

EXAMPLE 4

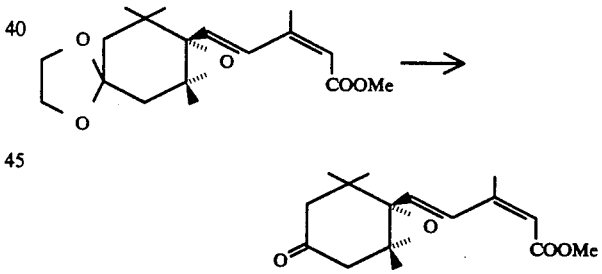

74 mg (0.23 mmol) of 4,4-ethylenedioxy-1-{4-(methoxycarbonyl)-3-methyl-1,3-butadien-1-yl}-1,2-oxo-2,6,6-trimethylcyclohexane was dissolved in 460 μl, of a 3% solution of perchloric acid in a THF/H$_2$O (1:1) mixture at 4° C. The obtained solution was stirred for 2 hours, neutralized with a saturated aqueous solution of sodium hydrogen-carbonate and extracted with methylene chloride. The organic layer was washed with water, dehydrated over anhydrous sodium sulfate and distilled in a vacuum to remove the solvent. 55 mg (86%) of 1-{4-(methoxycarbonyl)-3-methyl-1,3-butadien-1-yl}-1,2-oxo-2,6,6-trimethylcyclohexan-4-one was obtained.

$^1$H-NMR(CDCl$_3$): δ  1.07(s,3H),  1.15(s,3H), 1.27(s,3H),  1.97(d,1H,J=16),  2.04(d,3H, J=1.2), 2.59(d,1H,J=20),  2.63(d,1H,J=16),  2.86(d,1H,J=20), 3.71(s,3H),  5.75(brs,1H),  6.26(dd,1H,J=0.6,16), 7.74(dd,1H,J=0.7,16).

REFERENTIAL EXAMPLE 3

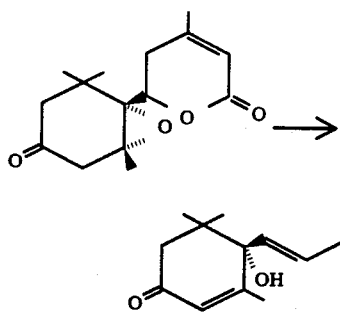

1.2 ml of a 10% solution of sodium hydroxide in an ethanol/pyridine (1:1) mixture was cooled with ice, followed by the addition of a solution of 1-(5,6-dihydro-2H-4-methyl-2-oxopyran-6-yl)-1,2-oxo-2,6,6-trimethylcyclohexan-4-one in 0.25 ml of pyridine. After 2 hours, the disappearance of the raw material was ascertained. The reaction mixture was diluted with diethyl ether and the pH thereof was adjusted to about 2 with 1M hydrochloric acid. The resulting mixture was extracted with diethyl ether. The organic layer was washed with a saturated aqueous solution of sodium chloride, dehydrated over anhydrous sodium sulfate and distilled in a vacuum to remove the solvent. 14 mg of a crude product was obtained. This crude product was purified by silica gel column chromatography (hexane/ethyl acetate=4:1) to give 5.3 mg (38%) of (+)-abscisic acid.

$^1$H-NMR(CDCl$_3$): δ 1.03(s,3H), 1.12(s,3H), 1.93(d,3H,J=1.3), 2.05(d,3H,J=1.1), 2.30(d,1H,J=17), 2.49(d,1H,J=17), 5.78(brs,1H), 5.97(brs,1H), 6.18(d,1H, J=16), 7.81(d,1H,J=16).

$[α]_D^{20}$: +383.7(C1.02, EtOH).

REFERENTIAL EXAMPLE 4

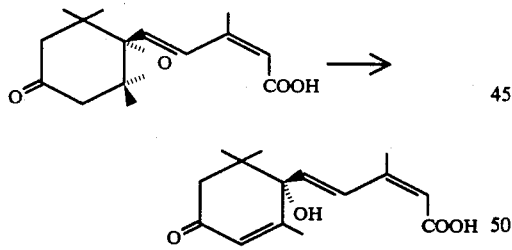

8.7 mg of 4-{4-(hydroxycarbonyl)-3-methyl-1,3-butadien-1-yl}-3,4-oxo-3,5,5-trimethylcyclohexan-1-one was dissolved in 2 ml of methanol, followed by the addition of 500 μl of 1N hydrochloric acid. The obtained mixture was stirred at room temperature for one hour, followed by the addition of a saturated aqueous solution of common salt. The obtained mixture was extracted with methylene chloride. The organic layer was washed with a small amount of a saturated aqueous solution of common salt, dehydrated over anhydrous sodium sulfate and distilled in a vacuum to remove the solvent. The residue was purified by silica gel column chromatography (hexane/ethyl acetate=4:1) to give 7.5 mg (87%) of objective (+)-abscisic acid.

$^1$H-NMR(CDCl$_3$): δ 1.03(s,3H), 1.12(s,3H), 1.93(d,3H,J=1.3), 2.05(d,3H,J=1.1), 2.30(d,1H,J=17), 2.49(d,1H,J=17), 5.78(brs,1H), 5.97(brs,1H), 6.18(d,1H, J=16), 7.81(d,1H,J=16).

$[α]_D^{20}$: +383.7(C1.02, EtOH).

REFERENTIAL EXAMPLE 5

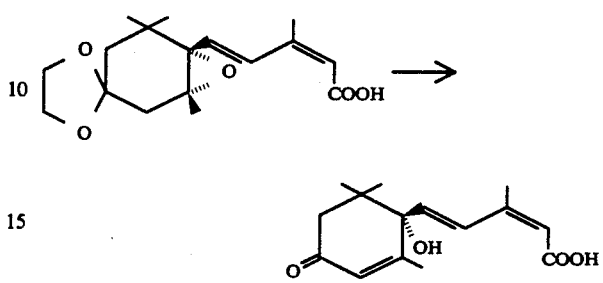

525 mg (1.703 mmol) of 4,4-ethylenedioxy-1-{4-(hydroxycarbonyl)-3-methyl-1,3-butadien-1-yl}-1,2-oxo-2,6,6-trimethylcyclohexane was dissolved in 16 ml of absolute methanol, followed by the addition of 3.6 ml of 1N hydrochloric acid. The obtained mixture was stirred at room temperature for 19 hours, followed by the addition of a saturated aqueous solution of common salt. The obtained mixture was extracted with methylene chloride. The organic layer was washed with a small amount of a saturated aqueous solution of common salt, dehydrated over anhydrous sodium sulfate and distilled in a vacuum to remove the solvent. The obtained crude product was recrystallized from a hexane/chloroform mixture to give 372 mg (83%) of (+)-abscisic acid.

REFERENTIAL EXAMPLE 6

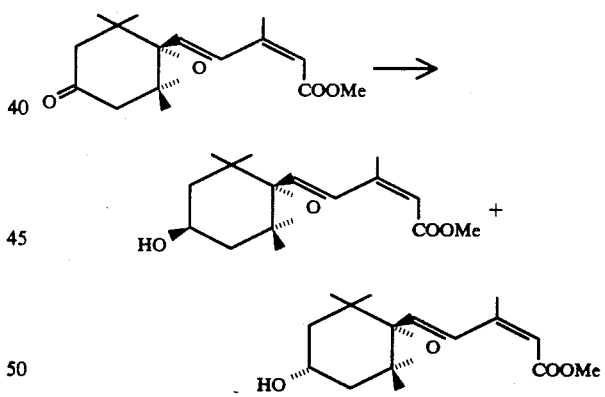

12 mg (1.6 equivalents) of lithium aluminum hydride was dissolved in 2 ml of anhydrous tetrahydrofuran in an argon atmosphere at 0° C., followed by the dropwise addition of a solution of 55 mg (0.198 mmol) of 1-{4-(methoxycarbonyl)-3-methyl-1,3-butadien-1-yl}-1,2-oxo-2,6,6-trimethylcyclohexan-4-one in 0.5 ml of anhydrous tetrahydrofuran. The obtained mixture was stirred for one hour. A saturated aqueous solution of ammonium chloride was added to the resulting mixture to neutralize excess reagent. The resulting mixture was extracted with diethyl ether. The organic layer was washed with a saturated aqueous solution of common salt, dehydrated over anhydrous sodium sulfate and distilled in a vacuum to remove the solvent. 52 mg (94%) of an objective mixture comprising two stereoisomers of 4-hydroxy-1-{4-(methoxycarbonyl)-3-methyl-1,3-butadien-1-yl}-1,2-oxo-2,6,6-trimethylcyclohexane was obtained. The isomer ratio was about 1:1.
4β-hydroxyl isomer ¹H-NMR(CDCl): δ 1.01(s,3H), 1.15(s,3H), 1.22(s,3H), 1.60~1.66(m,1H), 2.01(d,3H, J=1.2), 2.38(ddd,1H,J=1.7,5.0,14), 3.70(s, H), 3.59~3.64(m,1H), 5.70(brs,1H), 6.27(d,1H,J=16), 7.60(d,1H,J=16).
4α-hydroxyl isomer ¹H-NMR(CDCl₃): δ 1.04(s,3H), 1.16(s,3H), 1.22(s,3H), 1.36(ddd,1H,J=1.5,3.9,13), 1.90(dd,1H,J=8.4,15), 2.01(s,3H), 2.20(ddd,1H,J=1.3,6.7,15), 3.70(s,3H), 3.72~3.77(m,1H), 5.71(brs,1H), 6.20(d,1H,J=16), 7.62(d,1H,J=16).

REFERENTIAL EXAMPLE 7

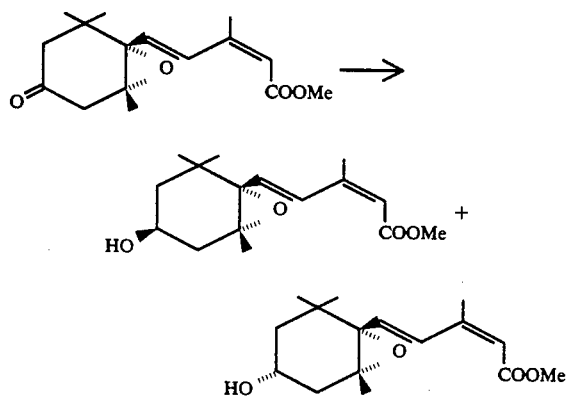

60 mg (0.216 mmol) of 1-{4-(methoxycarbonyl)-3-methyl-1,3-butadien-1-yl}-1,2-oxo-2,6,6-trimethylcyclohexan-4-one was dissolved in 570 μl of anhydrous tetrahydrofuran in an argon atmosphere at −78° C., followed by the dropwise addition of 432 μl (1 equivalent) of a 0.5M solution of K-SELECTRIDE® in tetrahydrofuran. The obtained mixture was stirred for 30 minutes, neutralized with a saturated aqueous solution of ammonium chloride and extracted with diethyl ether. The organic layer was washed with a saturated aqueous solution of common salt, dehydrated over anhydrous sodium sulfate and distilled in a vacuum to remove the solvent. The residue was purified by silica gel column chromatography (hexane/ethyl acetate=4:1) to give 23 mg (38%) of 4β-hydroxy-1-{4-(methoxycarbonyl)-3-methyl-1,3-butadien-1-yl}-1,2-oxo-2,6,6-trimethylcyclohexane and 7 mg (12%) of 4α-hydroxy-1-{4-(methoxycarbonyl)-3-methyl-1,3-butadien-1-yl}-1,2-oxo-2,6,6-trimethylcyclohexane.

REFERENTIAL EXAMPLE 8

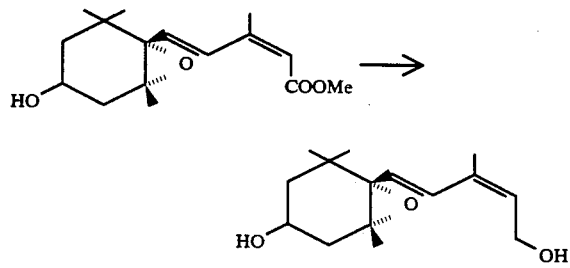

52 mg (0.186 mmol) of 4-hydroxy-1-{4-(methoxy-carbonyl)-3-methyl-1,3-butadien-1-yl}-1,2-oxo2,6,6-trimethylcyclohexane (4α-hydroxyl isomer/4β-hydroxyl isomer=1:1) was dissolved in 5 ml of anhydrous toluene in an argon atmosphere at −78° C., followed by the dropwise addition of 930 μl (5 equivalents) of a 1.0M solution of diisobutylaluminum hydride in hexane. After the obtained mixture had been reacted for one hour, methanol was added to the reaction mixture to neutralize excess reagent, followed by the addition of a saturated aqueous solution of ammonium chloride. The obtained mixture was extracted with diethyl ether. The organic layer was washed with a saturated aqueous solution of common salt, dehydrated over anhydrous sodium sulfate and distilled in a vacuum to remove the solvent. The residue was purified by silica gel column chromatography (hexane/ethyl acetate=4:1) to give 21 mg (48%) of 4-hydroxy-1-(5-hydroxy-3-methyl-1,3-pentadien-1-yl)-1,2-oxo-2,6,6-trimethylcyclohexane and 19 mg (44%) of its isomer.
α-diol isomer ¹H-NMR(CDCl₃): δ 1.01(s,3H), 1.15(s,3H), 1.19(s,3H), 1.36(ddd,1H,J=1.4,3.9,13), 1.89(dd,1H,J=8.5,15), 1.87(brs,3H), 2.20(ddd,1H,J=1.4,6.7,15), 3.84~3.91 (m,1H), 4.31(d,2H,J=6.9), 5.58(t,1H, J=6.9), 5.90(d,1H,J=16), 6.57(dd,1H, J=0.6,16).
β-diol isomer ¹H-NMR(CDCl₃): δ 0.98(s,3H), 1.14(s,3H), 1.19(s,3H), 1.24~1.27(m,2H), 1.60~1.66(m,1H), 1.87(d,3H,J=1.0), 2.38(ddd, 1H,J=1.8,5.1,14), 3.87,~3.94(m,1H), 4.29~4.34(m,2H), 5.57(t,1H,J=6.8), 5.96(d,1H,J=16), 6.56(dd,1H,J=0.6,16).

REFERENTIAL EXAMPLE 9

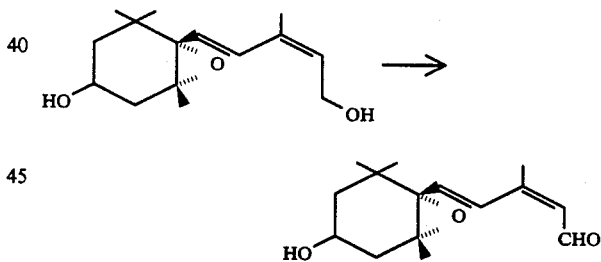

7 mg (0.024 mmol) of 4β-hydroxy-1-(5-hydroxy-3-methyl-1,3-pentadien-1-yl)-1,2-oxo-2,6,6-trimethylcyclohexane was mixed with 1 ml of anhydrous methylene chloride and 42 mg (20 equivalents) of manganese dioxide in an argon atmosphere. The obtained mixture was stirred at a room temperature for 2 hours and filtered to remove excess manganese dioxide. The filtrate was distilled in a vacuum to remove the solvent. 5 mg (83%) of xanthoxin was obtained. The α-diol isomer was also treated in a similar manner to that described above to give epixanthoxin.
(−)-xanthoxin ¹H-NMR(CDCl₃): δ 1.00(s,3H), 1.19(s,3H), 1.21(s,3H), 2.12(brs,3H), 3.87~3.96 (m,1H), 5.88(d,1H,J=8.2), 6.38(d,1H,J=15), 7.21(d,1H,J=15), 10.20(d,1H,J=8.2).
epixanthoxin ¹H-NMR(CDCl₃): δ 1.03(s,3H), 1.20(s,3H), 1.21(s,3H), 2.12(brs,3H), 3.86~3.95 (m,1H), 5.89(d,1H,J=8.1), 6.39(d,1H, J=15), 7.21(d,1H,J=15), 10.18(d,1H, J=8.2).

We claim:

1. An optically active epoxycyclohexanone represented by the formula:

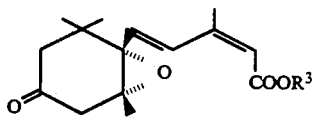

and an enantiomer thereof produced by the process comprising the steps of a) reacting an optically active aldehyde derivative represented by the general formula (1):

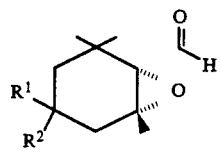

wherein $R^1$ and $R^2$ each represent a lower alkoxy group or together form a 1,3-dioxolane ring together with the carbon atom to which they are bonded, with a 3-methylcrotonic ester represented by the general formula (2):

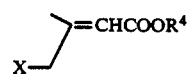

wherein $R^4$ represents a lower alkyl, allyl, aralkyl or aryl group; and X represents a chlorine, bromine or iodine atom, to produce an optically active epoxycyclohexane having an ester group represented by the general formula (3):

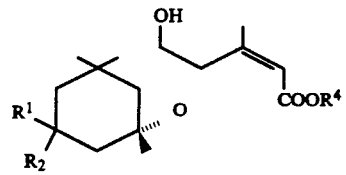

wherein $R^1$, $R^2$ and $R^4$ are the same as described above, b) treating the compound (3) with a solution of alkali metal alkoxide in solvent to produce an optically active epoxycyclohexane having a carboxyl group represented by the general formula (4):

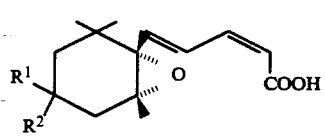

wherein $R^1$ and $R^2$ are the same as described above, and c) treating the compound (4) with perchloric acid under cooling to produce the objective epoxycyclohexanone.

* * * * *